(12) United States Patent
Yanagita et al.

(10) Patent No.: US 7,342,234 B2
(45) Date of Patent: Mar. 11, 2008

(54) RADIOLOGICAL IMAGING APPARATUS AND COOLING METHOD OF SAME

(75) Inventors: Norihito Yanagita, Hitachi (JP); Tsutomu Imai, Hadano (JP); Takashi Matsumoto, Hadano (JP); Kensuke Amemiya, Hitachinaka (JP); Yuuichirou Ueno, Hitachi (JP); Tomoyuki Seino, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/355,997

(22) Filed: Feb. 17, 2006

(65) Prior Publication Data

US 2006/0241386 A1    Oct. 26, 2006

(30) Foreign Application Priority Data

Mar. 31, 2005    (JP) ............................. 2005-105398

(51) Int. Cl.
    *G01T 1/24* (2006.01)
(52) U.S. Cl. .................................. 250/370.15
(58) Field of Classification Search ............ 250/370.15
    See application file for complete search history.

(56) References Cited

U.S. PATENT DOCUMENTS 6,586,744 B1 * 7/2003 Griesmer et al. ...... 250/370.09
6,621,084 B1   9/2003 Wainer et al.
2005/0067579 A1   3/2005 Tsuchiya et al.
2006/0186341 A1 * 8/2006 Ueno et al. ............ 250/363.05

FOREIGN PATENT DOCUMENTS

| JP | 04-157798 A | 5/1992 |
| JP | 09-275262 A | 10/1997 |
| JP | 10-160847 A | 6/1998 |
| JP | 2005-128000 A | 5/2005 |

* cited by examiner

*Primary Examiner*—David Porta
*Assistant Examiner*—Mark R Gaworecki
(74) *Attorney, Agent, or Firm*—Dickstein Shapiro LLP

(57) ABSTRACT

A radiological imaging apparatus which can keep detectors at a low temperature, improve a time resolution and an energy resolution and perform an accurate diagnosis is provided. In the radiological imaging apparatus, an imaging apparatus imaging a testing subject supported by a bed couples a detector board having placed thereon radiation detectors detecting radiations emitted from the testing subject and a signal processing board having placed thereon a signal processing circuit processing detection signals of the radiation detectors via an intermediate board by connectors, and separates a detector space including the radiation detectors and a signal processing circuit space including the signal processing circuit.

26 Claims, 9 Drawing Sheets

RADIOLOGICAL IMAGING APPARATUS AND COOLING METHOD OF SAME

BACKGROUND OF THE INVENTION

The present invention relates to a radiological imaging apparatus using radiations, and particularly relates to a radiological imaging apparatus, such as a positron emission computed tomographic apparatus (hereinafter referred to as "PET" apparatus), suitable for performing a radiographic inspection, and a cooling method of the radiological imaging apparatus.

An inspection technique using radiations can nondestructively inspect the inside of a testing subject. Particularly, radiographic inspection techniques for human bodies include X-ray CTs, PETs, single photon emission computed tomographic apparatuses (hereinafter referred to as "SPECT" apparatus) and the like.

Any of these techniques is a technique in which the physical quantity of an inspection object is measured as an integral value in a radiation traveling direction, and the integral value is back-projected, whereby the physical quantity of each voxel in the testing subject is calculated to form an image. In these techniques, it is necessary to process an enormous amount of data, and high-speed and detailed images have been provided with rapid development of computer technologies in recent years.

The PET and SPECT as radiological imaging apparatuses are methods capable of detecting functions and metabolism at a molecular biological level which cannot be detected by an X-ray CT or the like, and can provide functional images of a body. The PET is a method in which a radioactive agent labeled with a positron emission nuclear species such as $^{18}$F, $^{15}$O or $^{11}$C and the distribution thereof is measured to form an image. The agents include fluoro-deoxy-glucose (2-[F-18]fluoro-2-deoxy-D-glucose, 18FDG) and the like, and such an agent is used for identification of a tumor site making use of the fact that the agent is highly accumulated in a tumor tissue due to saccharometabolism.

A radiation nuclear species incorporated in the body decays to emit a positron (β+). The emitted positron emits a pair of annihilation γ-rays (annihilation γ-ray pair) each having energy of 511 keV when bonding to an electron to annihilate. Because this annihilation γ-ray pair is emitted in approximately opposite directions (180±0.6 degrees), projection data can be obtained by detecting the annihilation γ-ray pair at a time by a plurality of radiation detectors placed to surround the testing subject, and accumulating data in their emission directions. By back-projecting projection data (using a filtered back projection method or the like), an emission position (position at which the radiation nuclear species is accumulated) can be specified to form an image.

The SPECT is a method in which a radioactive agent labeled with a single photon emission nuclear species is administered, and its distribution is measured to form an image. A single γ-ray having energy of about 100 keV is emitted from the agent, and this single γ-ray is measured by the radiation detector. In measurement of the single γ-ray, the traveling direction of thereof can not be identified, and therefore in the SPECT, projection data is obtained by inserting a collimater in the front face of the radiation detector and detecting only a γ-ray from a specified direction. As in the PET, image data is obtained by back-projecting projection data using the filtered back projection method and the like. The SPECT is different from the PET in that no coincidence measurement is necessary due to measurement of a single γ-ray, and thus the number of radiation detectors is small, and so on, and the apparatus configuration is simple.

In the above described conventional radiological imaging apparatuses of the PET, the SPECT and the like, a scintillator is used as the radiation detector. The scintillator temporarily converts an incident γ-ray into visible light and then reconverts the visible light into an electric signal by a photomultiplier (photomul). The scintillator has a disadvantage that its energy resolution is low and an accurate diagnosis cannot necessarily be performed because the number of photons generated during conversion into visible light is small, and in addition, two-stage conversion processes are required as described above. Particularly, the deterioration in energy resolution is a cause of impossibility of quantitative evaluation during 3D imaging in the PET. That is because an energy threshold of the γ-ray must be reduced due to the low energy resolution, and body-interior scattering as noises increasing during 3D imaging is detected in a large amount.

Thus, in recent years, attention has been given to use of a semiconductor detector as the radiation detector for the radiological imaging apparatus. The semiconductor detector converts an incident γ-ray directly into an electric signal, and has a characteristic of a high energy resolution because of a large number of generated electrons and hole pairs.

Usually, characteristics such as a time resolution and an energy resolution in the scintillator and the semiconductor detector are known to deteriorate under a high-temperature environment, and as a measure against this, a radiological imaging apparatus comprising a cooling mechanism has been disclosed (see, for example, JP-A-10-160847 (all pages) and JP-A-9-276262 (all pages)

In the PET inspection, it is necessary to make a determination on coincidence (coincidence measurement) of detected events for detecting an annihilation γ-ray pair. Because fluctuations occur due to noises and the like of a radiation detector and a circuit system at a time of detection of the annihilation γ-ray pair, an acceptable specific coincidence time window is provided for making a determination on coincidence, and a determination is made based on the premise that two events detected in this coincidence time window are coincident.

For improvement of image quality and improvement of quantifiability of image information in the radiological imaging apparatus, characteristics of the time resolution and the energy resolution in the above described scintillator and semiconductor detector are improved.

If the characteristic of the time resolution is improved, the above described coincidence time window can be shortened. As a result, the probability of accidentally capturing γ-rays which are not a real annihilation γ-ray pair is reduced. The accidentally captured γ-ray pair (accidental coincidence event) does not retain real positional information, and therefore such noise components are eliminated, whereby image quality and quantifiability of image information are improved. If the characteristic of the energy resolution is improved, the γ-rays by body-interior scattering can be eliminated, and thus image quality and quantifiability of image information are improved.

However, in a situation in which with enhancement of the performance of the radiological imaging apparatus, the number and the density of radiation detectors are being increased, and with downsizing of the apparatus, the denseness of electronic circuit devices and the like incorporated therein is being increased, there are concerns that even if the above described conventional cooling mechanism is applied, heat generated from the electronic circuit device (signal processing circuit) including the radiation detector cannot sufficiently be cooled, and as a result, the characteristics of the time resolution and the energy resolution are deteriorated.

An object of the present invention is to provide a radiological imaging apparatus which can inhibit transmission of heat generated in the signal processing circuit to the radiation detector, improve the time resolution and the energy resolution, and perform an accurate diagnosis, and a cooling method of the radiological imaging apparatus.

SUMMARY OF THE INVENTION

For solving the above described problem, a radiological imaging apparatus of the present invention has a configuration in which an imaging apparatus imaging a testing subject supported on a bed has a unit board having radiation detectors, a signal processing circuit and an intermediate board, and a detector space which is formed in the imaging apparatus and in which the radiation detectors are placed, and a signal processing circuit space in which the signal processing circuit is placed are mutually separated by the above described intermediate board. According to this configuration, the signal processing circuit space in which the signal processing circuit having a heat generating element is placed, and the detector space in which the radiation detectors not generating heat but desired to be kept at a low temperature are placed can be isolated from each other by the intermediate board, and heat generated in the signal processing circuit can be inhibited from being transmitted to the radiation detectors. Thus, the quality of PET images is improved, thus making it possible to perform an accurate diagnosis.

Preferably, a coolant is fed by a cooling apparatus. The coolant may be fed from the detector space to the signal processing circuit space, or may be fed to the detector space and the signal processing circuit space separately. Further, it may be fed to only the signal processing circuit space having a heat generating element. By these configurations, a rise in temperature in the signal processing circuit space is inhibited, and a rise in temperature in the detector space on the radiation detector side is significantly inhibited.

Signals from a plurality of detector boards are processed by one signal processing board via the intermediate board, whereby signals from a plurality of detector boards can be covered by one signal processing board, thus increasing a degree of freedom of design.

The cooling method of the radiological imaging apparatus of the present invention comprises a step of separating the detector space in which the radiation detectors on the unit board are placed and the signal processing circuit space in which the signal processing circuit is placed, from each other, by the partition wall type intermediate board, and feeding a coolant to the signal processing circuit space. According to this method, the signal processing circuit space in which the signal processing circuit is placed can be cooled by the coolant, and the radiation detector can be kept at a low temperature.

The coolant may be fed to the detector space and the signal processing circuit space separately, or may be fed from the detector space to the signal processing circuit space after being fed to the detector space. In this case, by the coolant fed from the detector space to the signal processing circuit space, the radiation detector can efficiently be cooled, and the radiation detector can be kept at a low temperature.

A radiological imaging apparatus which can inhibit transmission of heat generated in the signal processing circuit to the radiation detector, improve the time resolution and the energy resolution, and perform an accurate diagnosis, and a cooling method of the radiological imaging apparatus are obtained.

Other objects, features and advantages of the invention will become apparent from the following description of the embodiments of the invention taken in conjunction with the accompanying drawings.

BRIEF DESCRIPTION OF THE DRAWINGS

FIG. 9 show an alternative example, wherein FIG. 9(a) is a sectional view of the detector unit when viewed from the front side, and FIG. 9(b) is a sectional side view thereof.

DESCRIPTION OF THE INVENTION

A radiological imaging apparatus as one preferred embodiment of the present invention will now be described in detail with reference to the drawings as appropriate. This embodiment will be described taking a PET apparatus as an example of an imaging apparatus constituting a radiological imaging apparatus. Of course, the present invention can be applied to not only radiological imaging apparatuses using a PET apparatus but also radiological imaging apparatuses using other imaging apparatuses such as a SPECT apparatus.

Embodiment 1

Figure 1:
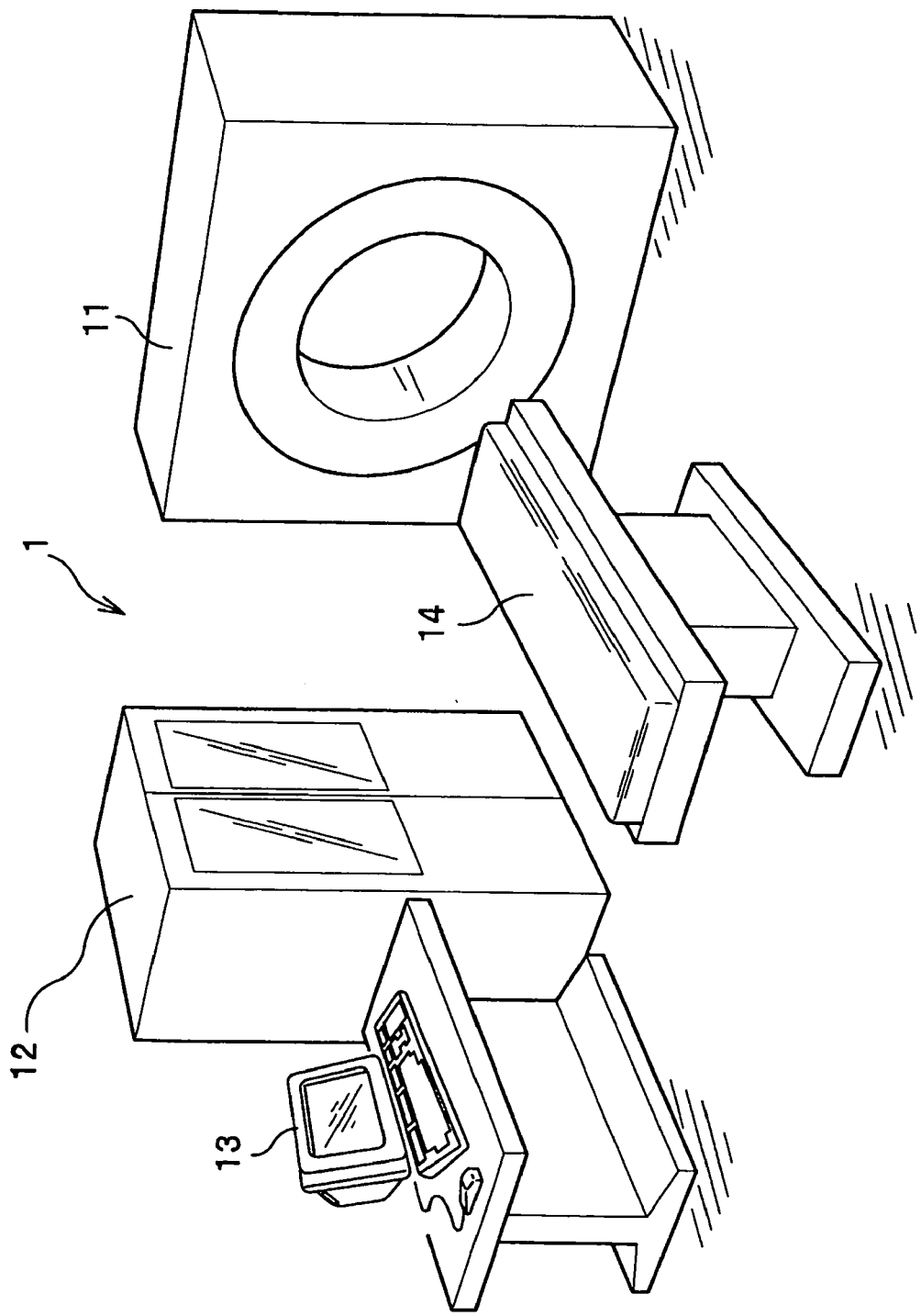
FIG. 1 is a perspective view showing the configuration of a radiological imaging apparatus according to embodiment 1.

First, the general configuration of the radiological imaging apparatus (PET apparatus 1) of this embodiment will be described with reference to FIGS. 1 and 2. The PET apparatus 1 comprises an imaging apparatus 11, a data processing apparatus 12 processing detection data obtained by imaging by the imaging apparatus 11 to convert the data into image data, a display apparatus 13 two-dimensionally or three-dimensionally displaying the image data output by the data processing apparatus 12, and a bed 14 forward-and-backward movably supporting a testing subject H (see FIG. 2) in the body axis direction.

The imaging apparatus 11 comprises detector units 2 having a large number of semiconductor radiation detectors (hereinafter referred to simply as detectors (FIGS. 3(a) and 3(B) and FIG. 4, the same will apply hereinafter), described in detail later) 21. As shown in FIG. 2, the detector units 2 are placed in a casing 11A of the imaging apparatus 11, and are placed in a large number along the circumferential direction with a body axis Z of the testing subject H substantially as a center such that they surround the bed 14 inserted in a space S of the imaging apparatus 11. The imaging apparatus 11 is further provided with a cooling apparatus 50 (some of its components are shown in FIG. 2).

A radioactive agent, for example fluoro-deoxy-glucose (FDG) containing 18F having a half life of 110 minutes is administered to the testing subject H. This radioactive agent is accumulated in, for example, an affected area C of cancer (FIG. 2). A pair of γ-rays (radiations) generated during annihilation of a positron emitted from the FDG is coincidentally emitted in a direction of 180±0.6 degrees from the inside of the testing subject H, as shown in FIG. 2. These γ-rays are detected by two detectors situated in directions opposite to each other by 180 degrees. An emission source of γ-rays (area in which the radiation agent is accumulated) in the body of the testing subject H is positioned based on detection signals output from these detectors 21.

Figure 2:
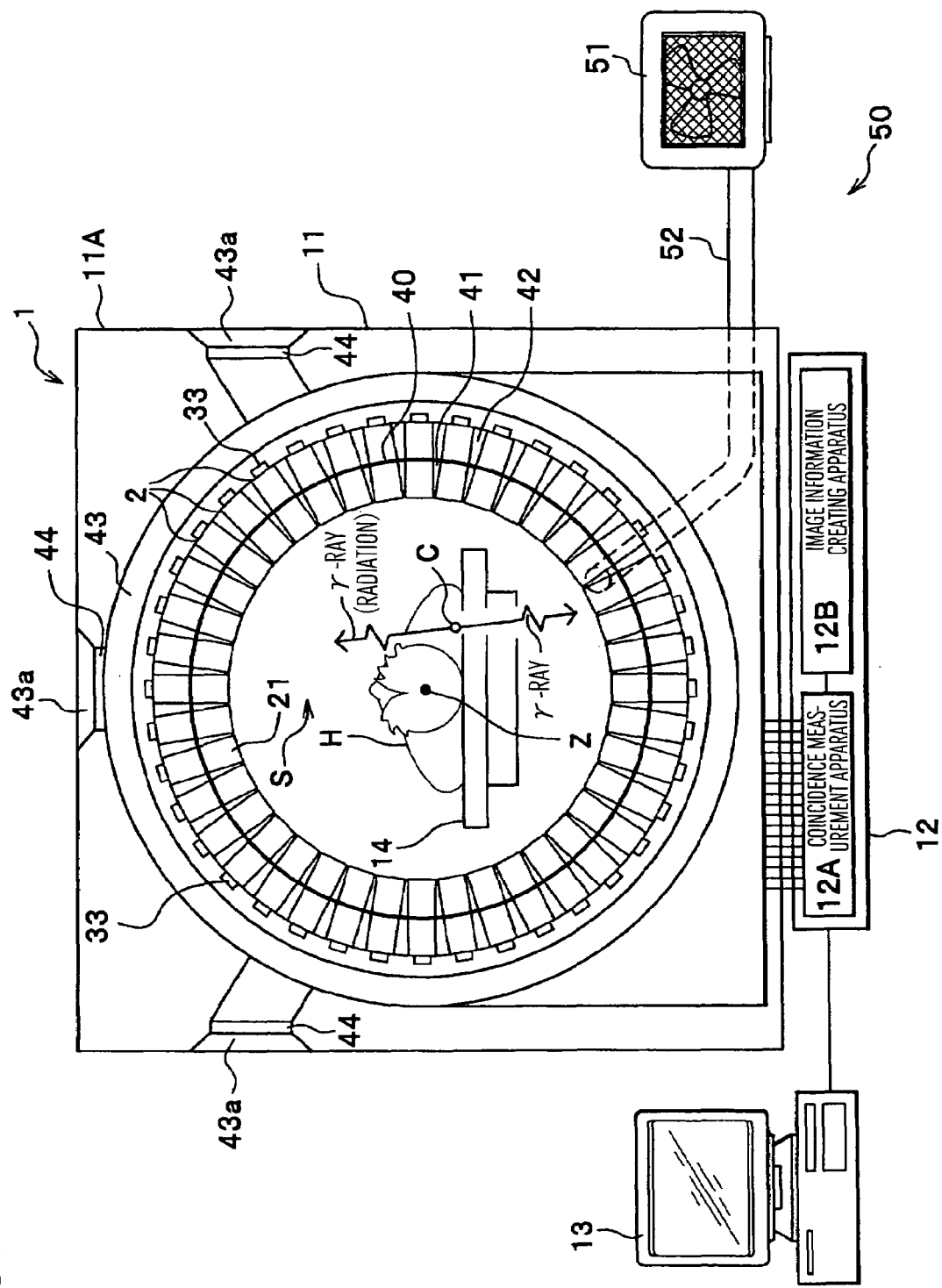
FIG. 2 schematically shows a cross-section along the circumferential direction of the imaging apparatus of FIG. 1.

The configuration of the detector units 2 and their periphery shown in FIG. 2 is shown schematically for the purpose of explaining their layout, and the detailed configuration will be described in detail later. The cooling apparatus 50 provided in the imaging apparatus 11 is intended for cooling the detectors 21 of the detector units 2. In this embodiment, air is used as a coolant (cooling medium) for cooling the detectors 21. The details of the cooling apparatus 50 will be described later.

As shown in FIG. 2, the data processing apparatus 12 has a coincidence measurement apparatus 12A and an image information creating apparatus 12B. The data processing apparatus 12 captures data (packet data described later) output from a coupling FPGA (field programmable gate array) 28 of a coupling board 22 (FIG. 3(b)) included in the detector unit 2. The coincidence measurement apparatus 12A performs coincidence counting using the captured data, thereby positioning a pair of detectors 21 detecting a pair of γ-rays generated by annihilation of one positron, and storing the positional information in a storage apparatus (not shown). The image information creating apparatus 12B creates PET image information (tomographic image information) for the testing subject H based on the specified positional information, and outputs the information to be displayed on the display apparatus 13.

Specifically, the coincidence measurement apparatus 12A compares detection time data of a plurality of detection data, and determines two data falling within a time window of coincidence counting (e.g. 10 ns) as an effective data pair. Further, the image information creating apparatus 12B uses each piece of detector positional information of the above described effective data pair to perform reconstruction of an image to create a PET image. The image information creating apparatus 12B outputs the created PET image to the display apparatus 13.

The details of main components will now be described.

First, the detection unit 2 will be described with reference to FIGS. 3(a) and 3(b). The detector unit 2 has a unit board 20 consisting of a plurality of boards housed in a housing 30 as a housing member. In this connection, the imaging apparatus 11 (see FIG. 2) has 60 to 70 detector units 2 detachably placed along the circumferential direction, and is adapted for easy maintenance inspection.

The unit board 20 has a detector unit 20A, a signal processing board 20B and an intermediate board 20C. The intermediate board 20C is placed between the detector board 20A and the signal processing board 20B. The detector board 20A and the signal processing board 20B are coupled to the intermediate board 20C via a connector C1 and a connector C2, respectively. As shown in FIG. 3(b), one detector unit 2 has 16 detector boards 20A, 8 signal processing boards 20B and one intermediate board 20C. The intermediate board 20C has therein a wiring (not shown) connected to the connector C1 and the connector C2. In the imaging apparatus 11, a plurality of detector boards 20A and a plurality of signal processing boards 20B are attached to the intermediate board 20C with the boards arranged such that they, respectively, orthogonally cross the direction of the body axis Z of the testing subject H (longitudinal direction of the bed 14) shown in FIG. 2, and among them, the signal processing boards 20B are housed in the housing 30.

The detector board 20A and the signal processing board 20B are mutually electrically coupled with each board substantially vertically to the intermediate board 20C, respectively, by the above described connectors C1 and C2 provided on both surfaces of the intermediate board 20C. Namely, by coupling the detector board 20A and the signal processing board 20B to the connectors C1 and C2 of the intermediate board 20C, respectively, a wiring (third wiring) provided in the intermediate board 20C is connected to a wiring provided in the detector board 20A (first wiring) and a wiring provided in the signal processing board 20B (second wiring) described later. In this embodiment, two detector boards 20A are electrically coupled to one signal processing board 20B, and both connectors C1 and C2 are closely placed at corresponding positions on both surfaces with the intermediate board 20C therebetween. Consequently, signals from two detector boards 20A can be transmitted to the signal processing board 20B with a low loss. In this connection, for example, the energy resolution as the detector 21 is improved as the loss becomes lower. Because two detector boards 20A are thus electrically coupled to one signal processing board 20B, the number of signal processing boards 20B is half of the number of detector boards 20A, and the signal processing boards 20B can be placed at intervals larger than intervals between detector boards 20A making effective use of a space within the housing 30. Namely, large spaces suitable for passing air as a coolant described later are formed between the signal processing boards B.

Electrical connections of the detector boards 20A and the signal processing boards 20B to the intermediate board 20C are made by the connectors C1 and C2, and therefore connection/cancellation of connection (coupling/cancellation of coupling) between boards is easy. Thus, for example, in the event that the detector 21, an analog ASIC 24, a digital ASIC 26 or the like described later becomes defective, only the detector board 20A or the signal processing board 20B in a defective part is replaced. Therefore, a wasteful situation in which the entire unit board 20 is replaced by new one because a part thereof is defective can be eliminated, and maintenance costs can be reduced.

The detector board 20A and the signal processing board 20B are configured to be coupled substantially vertically to the surface of the intermediate board 20C by inserting their one end into the connectors C1 and C2, respectively. Consequently, the accuracy of coupling of the detector board 20A to the intermediate board 20C is easily achieved, and the positional accuracy of the detector 21 mounted on the detector board 20A is easily achieved.

Figure 3:
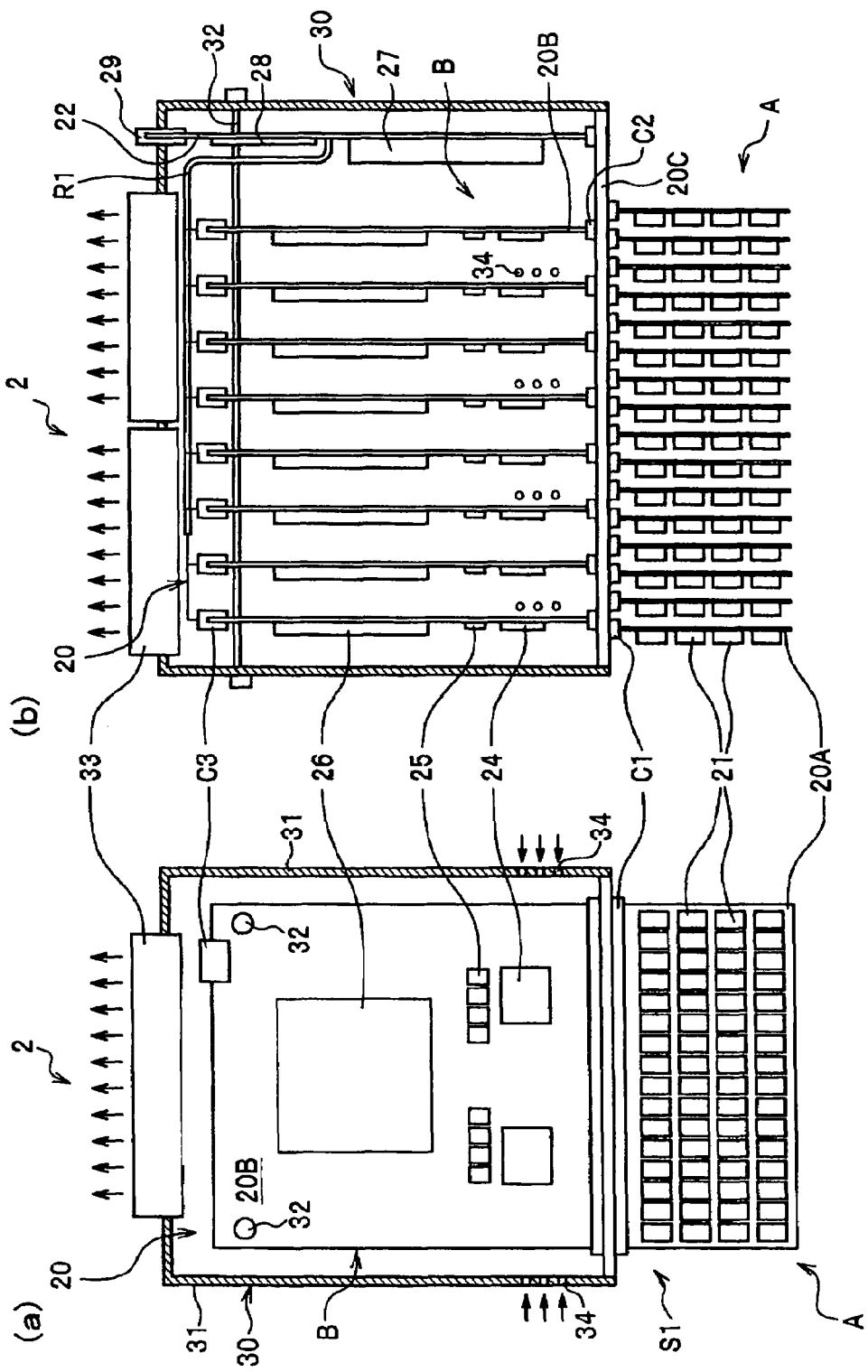
FIG. 3(a) is a sectional view of a detector unit for use in the radiological imaging apparatus according to the embodiment when viewed from the front side.
FIG. 3(b) is a sectional side view thereof.

The other end (upper end) of the signal processing board 20B is provided with a board connector C3, and as shown in FIG. 3(b), the unit board 20 is electrically connected to the coupling board 22 placed on the back side thereof (right side in FIG. 3(b)) and described later, by a link line R1 connected via the board connector C3.

As shown in FIGS. 3(a) and 3(b), a plurality of detectors 21 are placed in a grid form on one face of the detector board 20A. In this embodiment, total 64 detectors 21, i.e. 16 detectors along the circumferential direction of the imaging apparatus 11 (circumferential direction of space S, see FIG. 4) and 4 detectors along the radial direction of the imaging apparatus 11 (radial direction of space S, see FIG. 4), are provided per one surface. A plurality of detector units 2 are arranged to surround along the circumferential direction of the imaging apparatus 11 as described above, whereby the detectors 21 are placed to surround the body axis Z of the testing subject H. The detectors 21 are densely mounted on the detector board 20A with reduced arrangement pitches so that gaps between the detectors 21 are narrowed, whereby the denseness of the detectors 21 on the detector board 20A is increased. Thus, the efficient of detection of γ-rays on the detector board 20A is improved, and inspection time is reduced.

The detector 21 has a semiconductor member sandwiched between a cathode and an anode (not shown) and stacked. This semiconductor member is composed of single crystals of any of CdTe (cadmium telluride), TlBr (thallium bromide), GaAs (gallium arsenide) and the like. For the anode and the cathode, any material of Pt (palladium), Au (gold), In (indium) and the like is used. By making the detector 21 have such a structure, the efficiency of collection of electric charges is improved, the amount of γ-rays passing by can be reduced to increase interactions between the semiconductor member and the γ-ray (the number of counts) (increase the sensitivity). The detector 21 does not necessarily need to have such a stacked structure, but may have a single layer, or may have an appropriate layered structure. A wiring (not shown) connected to an electrode (e.g. anode) of each detector 21 is provided on the detector board 20A, and connected to the connector C1.

Figure 5:
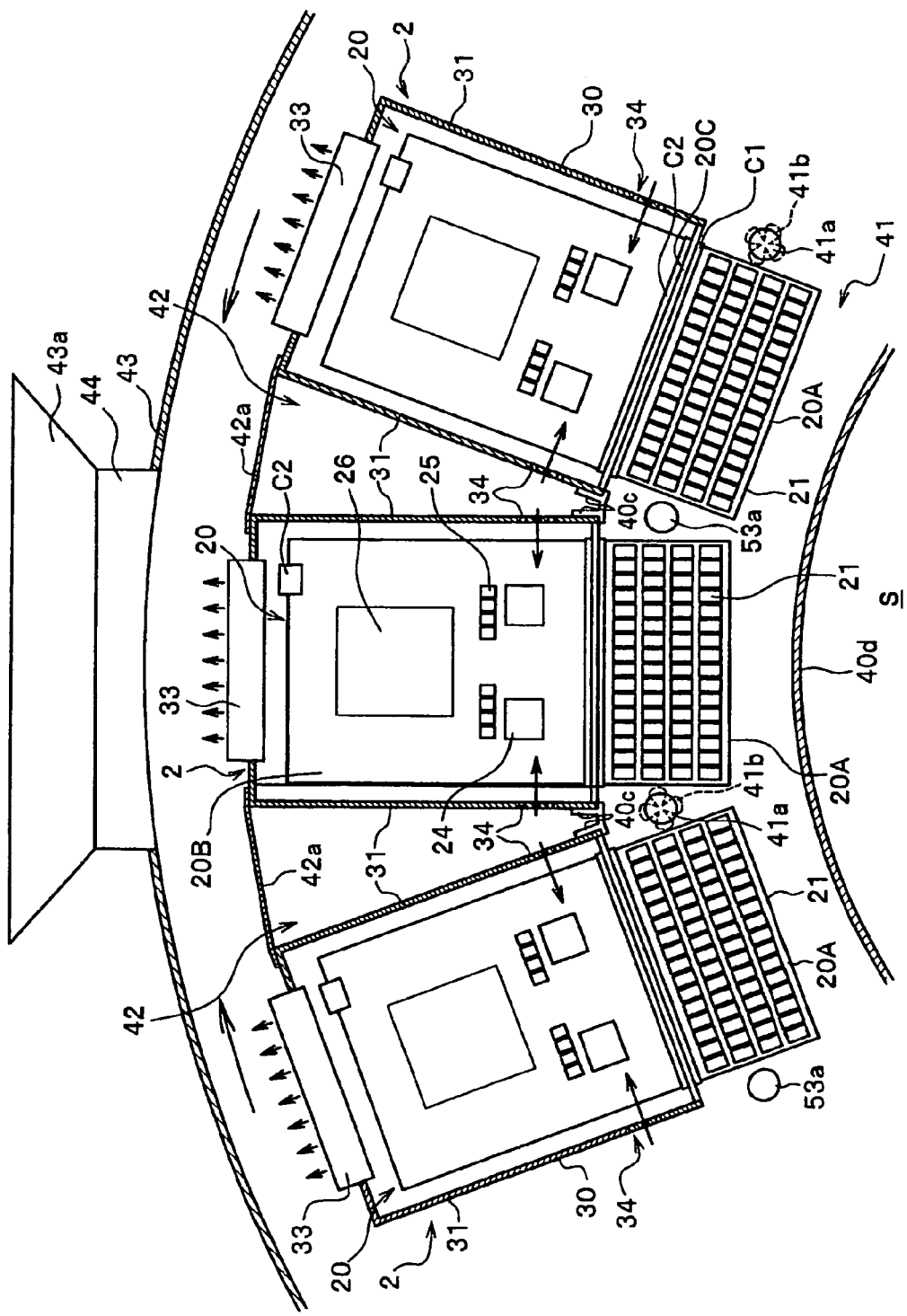
FIG. 5 is a sectional view showing a state in which the detector unit is mounted on the unit supporting portion.

In the PET apparatus 1, detection of the γ-ray is facilitated and the positional accuracy in detection of the γ-ray is improved as the number of detectors 21 placed is increased. Therefore, the detectors 21 are preferably densely placed as described above, and the detector units 2 are preferably placed closely in the circumferential direction in the casing 11A of the imaging apparatus 11 (see FIG. 2) as shown in FIG. 5. By employing such an arrangement structure, the positional resolution of the obtained image can be improved.

According to such a configuration, each detector 21 detects a γ-ray (radiation) of 511 keV for use in PET imaging, and outputs an analog signal (γ-ray detection signal) corresponding to energy of the γ-ray (energy causing an interaction with the semiconductor material). This γ-ray detection signal is sent to the signal processing board 20B by way of the connectors C1 and C2 through a wiring provided on the detector board 20A.

The signal processing board 20B will now be described. The signal processing board 20B is placed in the housing 30 with the signal processing board 20B attached substantially vertically to the surface of the intermediate board 20C via the connector C2 as described above, and has placed thereon integrated circuits (analog ASIC 24, ADC 25 and digital ASIC 26) as a signal processing circuit processing a γ-ray detection signal output in each detector 21 of the detector board 20A. In the signal processing board 20B, a wiring (not shown) connecting the analog ASIC 24, the ADC 25 and the digital ASIC 26 is provided on the signal processing board 20B. The wiring is connected to the connector C2. These integrated circuits to which weak γ-ray detection signals output from the detectors 21 have been input via the wiring provided on the detector board 20A, the connectors C1 and C2, and the signal processing board 20B amplify the γ-ray detection signals and measure energy of the detected γ-rays and the detection time. A preset detector ID is added to data of the measured energy and detection time, and the data is output as packet data (digital data). This output packet data is sent to the coupling FPGA 28 of the coupling board 22 from the board connector C3 through the link line R1.

The intermediate board 20C is detachably attached to the housing (housing member) 30 described later and seals a lower opening of the housing 30. Namely, in this embodiment, the intermediate board 20C constitutes the bottom wall of the housing 30. Consequently, the inside space of the housing 30 is separated from the outside space by the intermediate board 20C, and a signal processing circuit space B in which the signal processing board 20B is placed is formed in the housing 30.

A plurality of connecting wirings (not shown) for electrically connecting the connector C1 and the connector C2 are provided in the intermediate board 20C. An engaging raised portion (not shown) is provided on a predetermined side of the intermediate board 20C, and this engaging raided portion can engage with a groove portion (not shown) provided at the opening edge of the housing 30. By such engagement between the engaging raised portion and the groove portion, the intermediate board 20C is detachably attached to the housing 30.

As shown in FIG. 3(b), the coupling board 22 comprises a high-voltage electric power source 27 as a voltage increasing apparatus for supplying a voltage to each unit board 20, the coupling FPGA 28 integrating the above described packet data output through the board connector C3 of each unit board 20, and a data transferring apparatus 29 sending the integrated packet data to the data processing apparatus 12 (see FIG. 2). In this embodiment, the coupling board 22 is arranged in the same fashion as the signal processing board 20B, and placed on the back side of the housing 30 described later (right side in FIG. 3(b)). However, the present invention is not limited thereto, and the coupling board 22 may be placed on the front side of the housing 30 and the like.

The high voltage electric power source 27 is connected to a low-voltage electric power source (not shown) placed outside the imaging apparatus 11 (see FIG. 2), and a low voltage is increased to 300 V by a DC-DC converter and supplied to each detector 21. The high-voltage electric power source 27 is mounted on the coupling board 22 and placed in the housing 30, and therefore, as shown in FIG. 2, it can easily be placed in the imaging apparatus 11 by attaching the detector unit 2 to the unit supporting portion 40 as a support member.

In this embodiment, in the imaging apparatus 11, the unit boards 20 are placed along a direction in which the surface of the detector board 20A orthogonally crosses the Z direction of the body axis of the testing subject H, but the present invention is not limited thereto. For example, the surface of the detector board 20A may be faced toward the circumferential direction of the imaging apparatus 11.

The housing of the unit board 20 and the coupling board 22 in the housing 30 will now be described.

The housing 30 is a cylindrical body having a rectangular (preferably oblong) cross-section, and is circumferentially attached to the ring-shaped (cyclic) unit supporting portion 40 (see FIG. 4) provided in the casing 11A of the imaging apparatus 11. As shown in FIGS. 3(a) and 3(b), the housing 30 has a side part 31 formed to have a size for covering the signal processing board 20B of the unit board 20, and has an opening formed in the lower part as described above. Consequently, when the unit board 20 is placed in the housing 30, the signal processing board 20B of the unit board 20 is placed in the housing 30, but the entire detector board 20A, namely a part of the detector board 20A in which the detectors 21 are placed protrudes downward (outward) from the lower part of the housing 30. Namely, all the detectors 21 are situated outside the housing 30 without being covered with the housing 30. Therefore, as described later, in a state in which the detector unit 2 is mounted on the unit supporting portion 40, the detector 21 is placed with the detector 21 exposed to a first air passage 41 in the unit supporting portion 40.

In this embodiment, as described above, the boards are arranged in 16 lines along the depth direction (longitudinal direction of the bed 14) outside the housing 30 such that they are kept from overlapping, and the coupling board 22 is placed on the rear side of the housing 30. In the housing 30, the signal processing board 20B and the coupling board 22 are attached to the housing 30 by being supported in such a manner that they are pierced by four board fixation rods 32 extending along the longitudinal direction of the housing 30 (longitudinal direction of the bed 14) and provided in the housing 30.

A top part of the housing 30 is formed by bending the upper part of the side part 31 inward, an outlet for discharging a coolant is formed in this top part, and a unit fan 33 for discharging a gas is attached to this outlet. Namely, the unit fan 33 is provided opposite to a position which is opposite to the side on which the intermediate board 20C is placed in the signal processing circuit space B, and is away from the intermediate board 20C. This unit fan 33 includes a fan driven to rotate by a thin motor (not shown) and plays a role of discharging air in the housing 30 to an exhaust duct 43 (see FIG. 2) situated above the housing as described later. The unit fan 33 is actuated when supplied with electric power from a low-voltage electric power source (not shown) provided to the coupling board 22. The unit fan 33 is a continuous actuation type, but may be configured to be actuated when detecting that the temperature of the inside of the housing 30 has reached a predetermined temperature. By such a configuration, power consumption can be reduced.

The opening in the lower part of the housing 30 is sealed by the intermediate board 20C as described above, and the detector space A in which the detector board 20A is placed and the signal processing circuit space B in which the signal processing board 20B is placed are mutually separated with the intermediate board 20C therebetween. Thus, due to presence of the intermediate board 20C, the flow of air between the detector space A and the signal processing circuit space B through the opening in the lower part of the housing 30 is blocked. This prevents the situation in which air heated by heat from integrated circuits (digital ASIC 26 and the like) in the signal processing circuit space B flow into the detector space A to heat the detector 21. Thus, the detector 21 is not exposed to a high temperature.

A member capable of shielding against electromagnetic waves may be provided on the upper surface of the intermediate board 20C facing the signal processing circuit space B to protect the detector 21 from electromagnetic waves generated from integrated circuits (digital ASIC 26 and the like). Such a configuration enables the time resolution and the energy resolution of the detector 21 to the improved.

The side part 31 of the housing 30 is provided with a large number of air holes (inlets for coolant) 34 for introducing air as a coolant into the housing 30 from outside the housing 30. In this embodiment, the air holes 34 are situated near the intermediate board 20C, and specifically, they are situated on the side of the analog ASIC 24 of the signal processing board 20B. Namely, air introduced from the air holes 34 is fed to the analog ASIC 24 as a high heat generating source. As the unit fan 33 is driven, air present in a second air passage 42 outside the housing as described later is reliably introduced into the housing 30. The air introduced into the housing 30 is discharged to outside the housing 30 by the unit fan 33. Namely, the air introduced into the housing 30 is discharged to a side opposite to the side on which the detectors 21 are placed. In this embodiment, a plurality of air holes 34 are provided at predetermined intervals along the longitudinal direction of the housing 30. Consequently, a predetermined amount of air is substantially uniformly introduced into the housing 30.

As shown in FIG. 2, the detector unit 2 having such a housing 30 is attached to the unit supporting portion 40 placed in the casing 11A of the imaging apparatus 11. Namely, as shown in FIG. 4, the detector unit 2 is inserted from the detector 21 side into an opening 40a formed in the unit supporting portion 40 of the imaging apparatus 11, and detachably fixed with the lower end of the side part 31 of the housing 30 in close contact with a ring-shaped opening edge 40b of the unit supporting portion 40 (see FIGS. 4 and 5). At this time, the housing 30 has its lower end inserted into a fitting member 40c (see FIG. 5) provided on the outer surface of the opening edge 40b, and is thereby positioned. As shown in FIG. 4, the opening edge 40b is provided between openings 40a. A cylindrical plate 40d surrounding the space S is attached to the unit supporting portion 40 (see FIG. 4) with the cylindrical plate 40d situated inside the opening edge 40b. As described above, all the detectors 21 provided on all the unit boards 20 are situated outside the housing 30, and therefore when the detector unit 2 is attached to the opening 40a of the unit supporting portion 40, each detector 21 of the detector unit 2 is situated in the cyclic first air passage 41 formed between the unit supporting portion 40 and the cylindrical plate 40d. The detector unit 2 is fixed using a screw (not shown) or the like. Consequently, the detector unit 2 is detachably attached to the unit supporting portion 40. Thus, the advantage of easy maintenance or the like is obtained.

The detector unit 2 is attached to the unit supporting portion 40, namely in the imaging apparatus 11, the detector boards 20A and the signal processing boards 20B have their board surfaces (surfaces on which the detectors 21 and integrated circuits (analog ASIC 24 and the like) are placed) faced toward the longitudinal direction of the bed 14.

As shown in FIG. 5, the detector unit 2 does not have the side part 31 (see FIG. 3(a)) formed in the lower part (part situated inward from the unit supporting portion 40), and accordingly, the detector boards 20A of adjacent detector units 2 can be placed closely in the circumferential direction of the imaging apparatus 11. Consequently, the dead space between the detector boards 20A adjacent in the circumferential direction decreases, and the interval between the detectors 21 situated at the ends of these detector boards 20A and mutually adjacent is narrowed. Consequently, the sensitivity of detection of the γ-ray can be improved. Thus, inspection time can be reduced.

The cooling apparatus 50 will now be described. As shown in FIG. 4, the cooling apparatus 50 mainly comprises an air blowing apparatus 51, a duct 52, a flow divider 53 mounted on the back side of the above described unit supporting portion 40 and dividing the flow of air introduced through the duct 52, the first air passage (first coolant passage) of the unit supporting portion 40 into which the flow of air divided by the flow divider 53 is introduced, the second air passage 42 ((see FIG. 5, the same will apply hereinafter) second coolant passage) which is provided to surround the outside of the unit supporting portion 40 and into which air from the first air passage 41 is introduced, the exhaust duct 43 (see FIG. 5, the same will apply hereinafter) provided to surround the outside of the second air passage 42, and an exhaust fan 44 (see FIG. 5, the same will apply hereinafter) provided in the exhaust duct 43.

The air blowing apparatus 51 and the duct 52 are placed outside the casing 11A. The air blowing apparatus 51 is placed at a location such as the side or the rear of the imaging apparatus 11 such that the operation, maintenance and the like of the imaging apparatus 11 are not interrupted, air in a room where the imaging apparatus 11 is placed is suctioned by an included fan (not shown), and air is fed to the first air passage 41 inside the unit supporting portion 40 via the duct 52 and the flow divider 53. An air cleaning filter (not shown) is attached to the air intake port side of the air blowing apparatus 51, and air passing through this air cleaning filter is used as air for cooling. As the air cleaning filter, a HEPA (high efficiency particle air) filter having a high dust collection performance, an electric dust collection filter or the like may be used. The air blowing apparatus 51 may be provided with cooling means (not shown) for cooling air. In this case, a heat insulating material or the like for preventing dew formation is provided in the duct 52 and at other locations where air passes.

Figure 4:
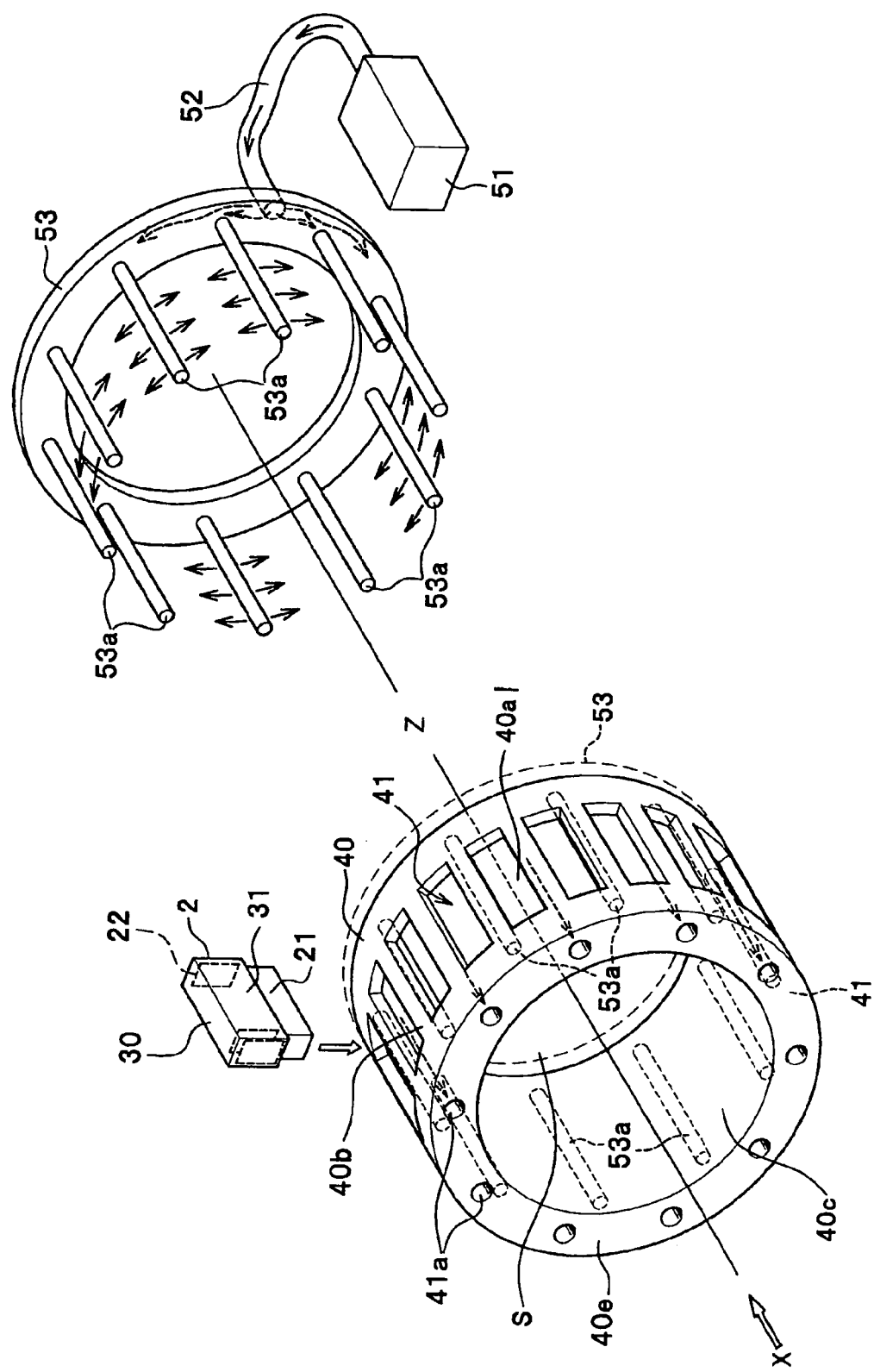
FIG. 4 is a perspective view showing an aspect in which the detector unit is mounted on a unit supporting portion of the imaging apparatus.

As shown in FIG. 4, the flow divider 53 comprises a plurality of rod-shaped blow portions 53a for blowing air fed from the duct 52. The blow portions 53a are provided extendedly in the back-and-forth direction (depth direction) of the unit supporting portion 40, and have a plurality of blow holes (not shown) for blowing air along the circumferential direction of the unit supporting portion 40. Insertion holes (not shown) into which the blow portions 53a can be inserted are provided on the back side of the unit supporting portion 40, and in a state in which the flow divider 53 is mounted on the unit supporting portion 40, the insertion holes are situated between the detector units 2 adjacent in the first air passage 41 as shown in FIG. 5. Consequently, air blown from the blow portion 53a passes between the detector boards 20A, and cools each detector 21 mounted on each detector board 20A. In this embodiment, the blow portions 53a are placed between the detector units 2 alternately.

The cyclic first air passage 41 is formed between the opening edge 40b and the cylindrical plate 40d as described above. The second air passage 42 is formed outside the unit supporting portion 40 and between the housings 30. The first air passage 41 and the second air passage 42 are formed in the casing 11A, and the exhaust duct 43 and the exhaust fan 44 are provided in the casing 11A.

In the first air passage 41, the detector boards 20A of the unit board 20 are placed at predetermined intervals in the circumferential direction as shown in FIG. 5. The flow divider 53 is mounted (shown with broken lines in FIG. 4) on the back surface part of the unit supporting portion 40 as described above, and a plurality of passage holes 41a communicating with the first air passage 41 are provided on a front surface part 40e of the unit supporting portion 40 as shown in FIG. 4. The passage holes 41a are provided such that they are situated between the detector units 2 on the side of the above described flow divider 53 where the blow portion 53a is not placed when viewed from the direction indicated by the arrow X in FIG. 4. Consequently, air blown from the blow portion 53a of the flow divider 53 passes between the detector boards 20A, and is then discharged from the passage hole 41a. As shown in FIG. 5, a small exhaust fan 41b may be provided at a position near the passage hole 41a.

The passage hole 41a communicates with the second air passage 42, whereby air from the first air passage 41 is introduced into the second air passage 42.

As shown in FIG. 5, the second air passage 42 is formed by air isolated by the side parts 31 of adjacent housings 30, a top plate 42a running between the housings 30, and the opening edge 40b of the unit supporting portion.40, and situated between the detector units 2. In a part of the second air passage 42 communicating with the passage hole 41a, a passage (not shown) for introducing air from the passage hole 41a into the second air passage 42 is formed in the casing 11A. The opening of the second air passage 42 on the back side (between the side parts 31 and 31 at the rear end of the housing 30), which is opposite to the aforementioned part, is closed by a plate member (not shown). When one of the detector units 2 is removed from the unit supporting portion 40 for maintenance operations and the like, it can easily be removed by removing the top plate 42a, the plate member (not shown) and the like attached to the detector unit 2 to be removed. Thus, maintenance operations and the like can easily be performed without necessity of complicated operations such as removal of the entire second air passage 42.

The second air passage 42 communicates with the inside of the housing 30 through a plurality of air holes 34 provided on the side part 31 of the housing 30. Consequently, air from the second air passage 42 is introduced into the housing 30 along with the driving of the unit fan 33 of the housing 30. The exhaust duct 43 communicates with the inside of the housing 30 via the unit fan 33, and by the driving of the unit fan 33, air from the inside of the housing 30 is discharged into the exhaust duct 43. The exhaust duct 43 is provided with total three air exhaust ports 43a formed in a room where the imaging apparatus 11 is placed (see FIG. 2), and air in the exhaust duct 43 is discharged into the room through the exhaust fan 44 provided each air exhaust port 43a.

In this embodiment, air in the room where the imaging apparatus 11 is placed is suctioned, used for cooling and discharged into the room again after cooling, but air may be suctioned from outside the room, and discharged to outside the room again after cooling.

Such cooling by the cooling apparatus 50 will now be described. When an electric power switch (not shown) of the imaging apparatus 11 is operated to supply electric power to the imaging apparatus 11, the air blowing apparatus 51 is actuated in synchronization with actuation of the imaging apparatus 11. Then, air in the room is fed as air for cooling from the air blowing apparatus 51 to the first air passage 41 of the unit supporting portion 40 via the duct 52 and the flow divider 53 (step of feeding the coolant (air for cooling) to the detector space A), and the fed air passes between the detector boards 20A placed in the first air passage 41. In the first air passage 41, the detectors 21 of the unit board 20 held by the detector unit 2 is placed in an exposed state, and therefore the detectors 21 are cooled by air fed into the first air passage 41. The detector 21 does not fundamentally generate heat as its nature, but even in the event that for example, heat from the signal processing board 20B is transmitted via the connectors C1 and C2 as coupling parts, the detector 21 can significantly be inhibited from being heated by the heat. Thus, the time resolution and the energy resolution of the detector 21 can be improved.

Thereafter, air passing through the first air passage 41 is introduced into the second air passage 42 through the passage hole 41a, and introduced into the signal processing circuit space B in the housing 30 through the air hole 34 provided in the side part 31 of the housing 30 (step of feeding the coolant (air for cooling) fed to the detector space A from the detector space A to the signal processing circuit space B). Consequently, the inside of the housing 30 is cooled by air, the integrated circuits (digital ASIC 26 and the like) are cooled, and a rise in temperature of the signal processing circuit space B can be inhibited to prevent the thermal runway of the signal processing system. Thus, the reliability of the apparatus is improved.

Thus, since air for cooling is fed to the signal processing circuit space B from the detector space A in which the detectors 21 are placed, and the integrated circuits (digital ASIC 26 and the like) is cooled by the air which has cooled the detectors 21, the detectors 21 and the integrated circuits (digital ASIC 26 and the like) are efficiently cooled in a series of flows. The amount of air fed by the air blowing apparatus 51 is set so that cooling can be performed within the bounds not causing the thermal runaway and the element-destruction of the integrated circuits (digital ASIC 26 and the like) and the detectors 21 are kept at a low temperature with consideration given to the number of detectors 21 (numerical quantity of unit boards 20), the temperature rise situation of the integrated circuits (digital ASIC 26 and the like) and the like.

Air fed into the housing 30 is forcefully discharged to the exhaust duct 43 by the unit fan 33. The post-cooling air discharged to the exhaust duct 43 is discharged from the air exhaust port 43a into the room by the exhaust fan 44 provided at the air exhaust port 43a. In the manner described above, cooling by the cooling apparatus 50 using air is performed.

The detector 21 having CdTe used in this embodiment as a semiconductor material responds to light to generate electric charges, and therefore shielded against light so that no external light enters to illuminate the detector 21. Specifically, the housing 30 and the unit supporting portion 40 shown in FIG. 4 are composed of a material having a light blocking effect such as aluminum or an aluminum alloy, and configured to eliminate gaps through which light enters, including areas where both the components fit together.

As shown in FIG. 5, for light entering from the direction of the space S, light can reliably be prevented from arriving at the detector 21 by placing the cylindrical plate 40d so that its outer peripheral surface is situated near the free end (lower end) of the detector board 20A. The light blocking effect can be improved by forming the cylindrical plate 40d from an aluminum alloy (or aluminum). As another method for blocking light entering from the direction of the space S, the housing 30 may be covered with a light blocking cover or the like (not shown), or the detector 21 may be coated with a light blocking material so that a light blocking film is formed, instead of the light blocking cover or the like.

The exhaust duct 43 may be divided to be sectioned in the circumferential direction, and each space of the exhaust duct 43 sectioned may be provided with the exhaust fan 44. By providing the exhaust fan 44 independently in this manner, more efficient discharge of air can be performed, and smooth passage of air can be achieved. The exhaust duct 43 may be divided into two sections or four or more sections.

Effects in this embodiment will be described below.

(1) According to the radiological imaging apparatus, the unit board 20 has the detector board 20A on which the detectors 21 are placed, the signal processing board 20B on which the signal processing circuit is placed, and the intermediate board 20C existing between the detector board 20A and the signal processing board 20B with both the boards coupled via connectors C1 and C2 on both surfaces, respectively, and the detector space A which is formed in the imaging apparatus 11 and in which the detectors 21 are placed and the signal processing circuit space B in which the signal processing board 20B is placed are mutually separated by the intermediate board 20C, and therefore heat generated by the integrated circuits (digital ASIC 26 and the like) is blocked by the intermediate board 20C, and can significantly be inhibited from being transmitted to the detector 21 side. Consequently, a rise in temperature of the detectors 21 present in the detector space A can significantly inhibited, and the detectors 21 can be kept at a low temperature. Consequently, the time resolution and the energy resolution can be improved. Because the time resolution can be improved, the coincidence time window of the γ-ray can be decreased, and thus the probability of accidentally capturing the γ-ray is reduced. Further, because the energy resolution can be improved, body-interior scattering is eliminated (noises are reduced). Thus, a radiological imaging apparatus which can perform an accurate diagnosis with the quality of PET images and the quantifiability improved is obtained.

Moreover, because the detector board 20A and the signal processing board 20B are coupled via the connectors C1 and C2, heat from the signal processing board 20B side is hard to be transmitted directly to the detector board 20A side, thus making it possible to significantly inhibit a rise in temperature of the detectors 21 placed on the detector board 20A. Consequently, a radiological imaging apparatus with a further improved time resolution and energy resolution is obtained.

Because a rise in temperature of the detectors 21 can be inhibited, a change in the detector 21 with time can be inhibited to reduce a failure rate. Thus, characteristics of the detector 21 are stabilized, the reliability of the imaging apparatus 11 is improved, and running costs can be reduced.

Further, because the detector 21 is kept at a low temperature, an advantage of stabilizing voltages supplied from the high-voltage electric power source 27 of the coupling board 22 is also obtained.

Moreover, because the detector board 20A and the signal processing board 20B are electrically connected via the connectors C1 and C2 by the intermediate board 20C, and signals from two detector boards 20A are processed by one signal processing board 20B via the intermediate board 20C, the number of signal processing boards 20B can be reduced to half the number of detector boards 20A, thus increasing the degree of freedom of design.

Because the area where the detectors 21 are present is situated outside the housing 30, a rise in temperature of the detector 21 can more effectively inhibited by the intermediate board 20C.

Further, because the unit board 20 has the detector board 20A and the signal processing board 20B attached to the intermediate board 20C, the detector board 20A may be formed to have only a size for mounting the detectors 21, thus making it possible to downsize the detector board 20A. Thus, it is relatively simple to hold the detector board 20C vertical to the surface of the intermediate board 20C, whereby the positional accuracy of the detectors 21 can be improved.

Because the detector space A and the signal processing circuit space B are separated via the intermediate board 20C, the boards can freely be laid out in the spaces A and B. Consequently, on the detector space A side, the detector boards 20A can be mutually closely placed, and the detectors 21 can be mutually closely placed. Thus, a radiological imaging apparatus which can perform an accurate diagnosis with the sensitivity of detection of the γ-ray improved is obtained.

(2) Since the detector board 20A and the signal processing board 20B can be coupled to the intermediate board 20C attached to the housing to fix the detector board 20A to the intermediate board 20C, the detector board 20A can accurately be held, and the positional deviation of the detector board 20A can be prevented. Therefore, the position of the detector 21 can be known correctly, and the precision of PET images is improved.

If the detector board 20A and the signal processing board 20B are directly coupled by a connector without using the intermediate board 20C, the length of the coupled board increases, and therefore even a small angular deviation will cause a large positional deviation of the detector 21. In this embodiment, the detector board 20A is attached to the intermediate board 20C as described above, and therefore a distance between the support point (connector C1) of the detector board 20A and the front end of the detector board 20A decreases. This can significantly improve the accuracy of the positions at which the detectors 21 provided on the detector board 20A are arranged. Therefore, clear PET images can be obtained.

If the detector board 20A and the signal processing board 20B are directly coupled by the connector, they are coupled such that the end of the detector board 20A is superimposed on the end of the signal processing board 20B at the coupled portion. Therefore, the thickness at the coupled portion increases, and the interval between the detectors 21 in the longitudinal direction of the bed increases. Accordingly, the spatial resolution in the longitudinal direction of the bed is degraded. In this embodiment, because the detector board 20A is attached to the intermediate board 20C, the interval between the detectors 21 adjacent in the longitudinal direction of the bed can be reduced, and the spatial resolution in the longitudinal direction of the bed can be improved.

(3) According to the radiological imaging apparatus, the detector space A and the signal processing circuit space B can suitably be cooled by air fed by the cooling apparatus 50. Moreover, because air is fed from the detector space A to the signal processing circuit space B by the cooling apparatus 50, the detector 21 side having no heat generating elements and having a lower temperature is cooled, and then the integrated circuit (digital ASIC 26 and the like) side having heat generating elements and having a higher temperature is cooled. Therefore, a rise in temperature of the detectors 21 can still further be inhibited along with the effect of inhibition of a rise in temperature of the detectors 21 by the intermediate board 20C described above.

(4) According to the radiological imaging apparatus, the unit board 20 is housed in the housing 30 to construct the detector unit 2, and a plurality of detector units are placed in the circumferential direction of the ring-shaped unit supporting portion 40 into which the bed 14 supporting the testing subject H is inserted, and dense implementation of the detectors 21 can be achieved, and a radiological imaging apparatus with the spatial resolution improved and with the inspection time reduced by a substantial improvement in sensitivity is obtained. Particularly, because the part of the detector board 20A where the detectors 21 are present is placed outside the housing 30, the interval between the detector boards 20A of adjacent detector units 2 can be reduced, and the detectors 21 can be placed more densely in the circumferential direction of the imaging apparatus 11. Thus, the sensitivity of detection of the γ-ray in the imaging apparatus 11 is improved, and the inspection time can be reduced.

Figure 7:
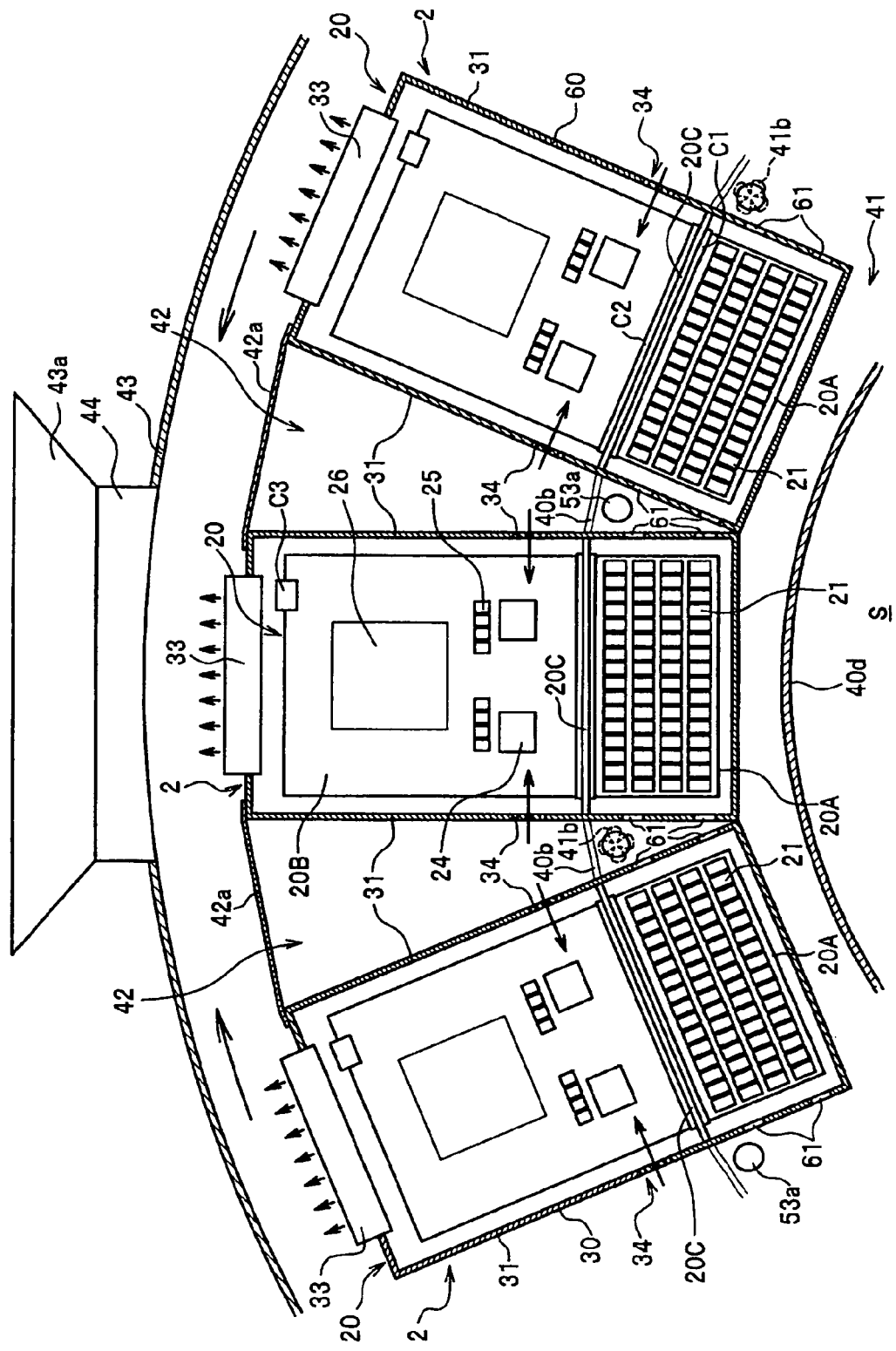
FIG. 7 is a sectional view showing a state in which the detector unit is mounted on the unit supporting portion.

The part of the detector board 20A where the detectors 21 are present is placed outside the housing 30, the efficient of cooling of the detectors 21 is improved compared to the configuration of FIG. 7.

Because the detection unit 2 is held by the unit supporting portion 40 to be fixed, attachment/detachment of the detector unit 2 is easy, and maintainability is high.

(5) According to the radiological imaging apparatus, the detector space A in which the detectors 21 are placed and the signal processing circuit space B are mutually separated by the intermediate board 20C, and the detectors 21 are placed in an exposed state in the lower part of the detector unit 2, and therefore a radiological imaging apparatus with a further improved time resolution and energy resolution of the detectors 21 is obtained.

(6) According to the radiological imaging apparatus, the first air passage 41 for cooling the detectors 21 is formed in the unit supporting portion 40, and therefore the unit supporting portion 40 can effectively used as a passage for feeding air, and a mechanism for cooling can be made simple.

(7) According to the radiological imaging apparatus, semiconductor radiation detectors are used as the detectors 21, and therefore the energy resolution is improved, and γ-rays resulting from body-interior scattering can be removed. Particularly, during 3D imaging, an increase in γ-rays resulting from body-interior scattering is inhibited, the quality of PET images can be improved, and quantifiable inspection is possible.

(8) According to the radiological imaging apparatus, semiconductor radiation detectors are used as the detectors 21, and therefore positional resolution is improved. In the conventional scintillator, the positional resolution is easily degraded because signals of several tens of scintillators are amplified by one photomul, and a detected scintillator position is calculated using calculation of the center of gravity. Because the photomul is used, miniaturization of scintillators is limited.

In the radiological imaging apparatus of this embodiment, an amplification circuit is formed for each detector 21, and therefore the positional resolution is not degraded. Further, because of use of a signal processing circuit using ASIC (24, 26) and the like, miniaturization of detectors 21 is easy, and further improvement of the positional resolution is possible.

(9) In the radiological imaging apparatus, semiconductor radiation detectors 21 are used as the detectors 21 and ASIC (24, 26) is used for processing signals thereof, and therefore downsizing of the periphery of the detectors 21 is achieved compared to the photomul used in the scintillator. Thus, upsizing of the first air passage 41 can be prevented, and the imaging apparatus 11 can be downsized although it has the cooling apparatus 50. Because the detectors 21 and the integrated circuits (digital ASIC 26 and the like) are arranged orderly on the unit board 20, the detector unit 2 can be downsized, the second air passage 42 can also be downsized accordingly, and the imaging apparatus 11 can be downsized although it has the cooling apparatus 50.

(10) The unit supporting portion 40 is a member supporting the detector unit 2, and also a member separating the first air passage 41 and the second air passage 42. Therefore, it is not necessary to provide a member supporting the detector unit 2 and a member separating the first air passage 41 and the second air passage 42 separately, thus making it possible to simplify the structure of the imaging apparatus 11. The intermediate board 20C plays a role of not only separating the detector space A and the signal processing circuit space B but also separating the first air passage 41 and the second air passage 42. The provision of the intermediate board 20C further simplifies the structure of the imaging apparatus 11.

Embodiment 2

Figure 6:
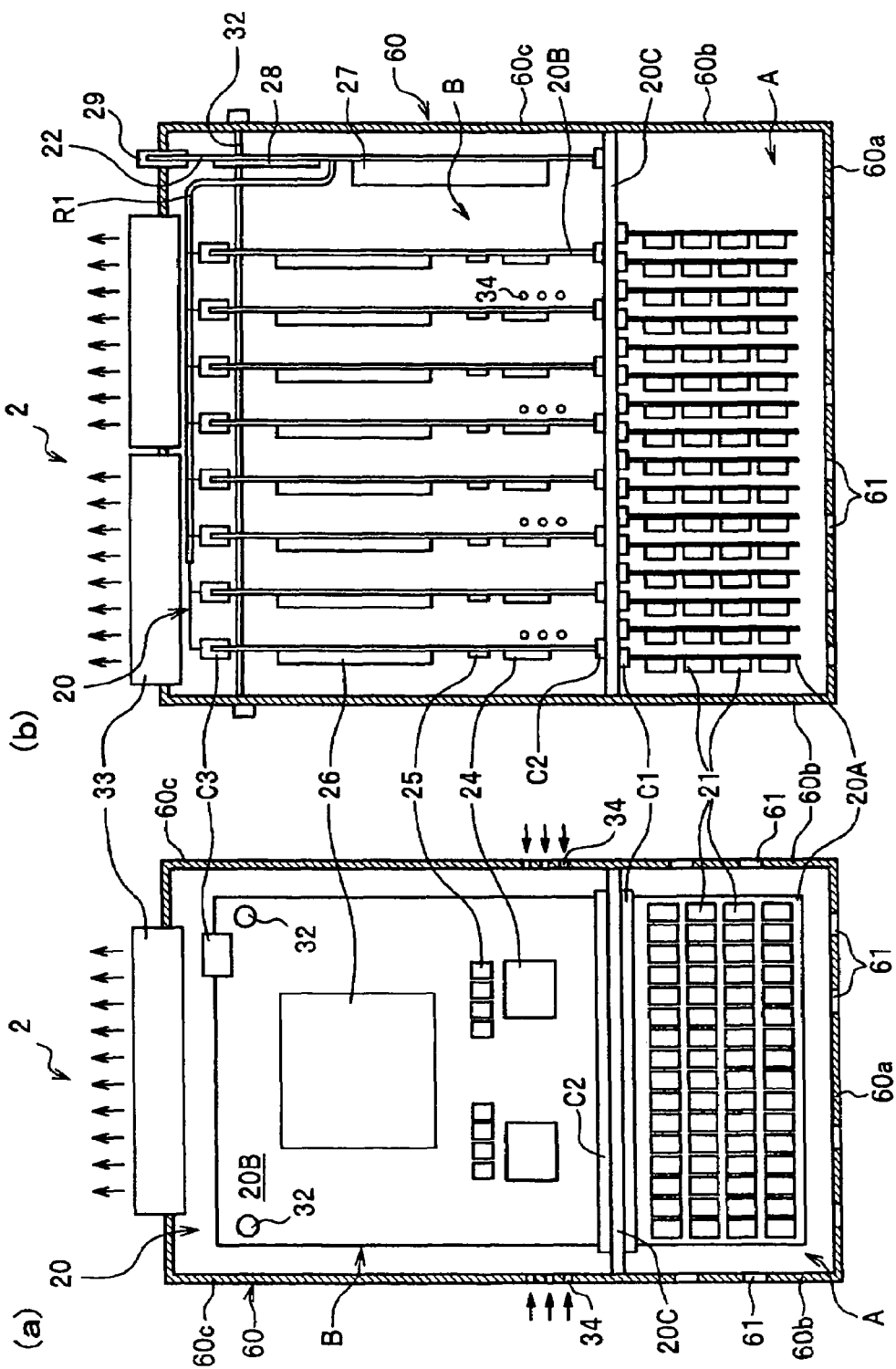
FIG. 6(a) is a sectional view of a detector unit for use in the radiological imaging apparatus according to embodiment 2 when viewed from the front side.
FIG. 6(b) is a sectional side view thereof.

The PET apparatus 10 as the radiological imaging apparatus which is another embodiment will be described. The radiological imaging apparatus of this embodiment is different from embodiment 1 in that a housing 60 as a housing member for the detector unit 2 is formed to have a size for covering the entire unit board 20 as shown in FIGS. 6(a) and 6(b) and FIG. 7. Specifically, as shown in these figures, the housing 60 has a box-like shape having a bottom part 60a, and has no opening provided in the lower part unlike the housing 30 described in embodiment 1 (see FIGS. 3(a) and 3(b)). Namely, in the housing 60, the detector space A and the signal processing circuit space B separated by the intermediate board 20C are formed. The bottom part 60a and a side part 60b forming the detector space A of the housing 60 is provided with an air hole 61 communicating with the first air passage 41.

In this embodiment, the lower part of the housing 60 is placed in the first air passage 41, whereby air fed to the first air passage 41 naturally flows into the detector space A through the air hole 61, whereby the detectors 21 are cooled. The housing 60 is also cooled at the same time by air fed to the first air passage 41, and a rise in temperature of the detectors 21 is effectively inhibited. The first air passage 41 communicates with the second air passage 42 via the passage hole 41a (see FIG. 4) as in embodiment 1, and air which has passed through the first air passage 41 is fed to the second air passage 42 through the passage hole 41a.

A side part 60c sectioning the signal processing circuit space B of the housing 60 is situated in the second air passage 42, and the second air passage 42 communicates with the signal processing circuit space B in the housing 60 through the air hole 34 formed in the side part 60c. Consequently, air fed to the second air passage 42 is fed to the signal processing circuit space B through the air hole 34. Air fed to the signal processing circuit space B is discharged into the exhaust duct 43 by the unit fan 33 provided in the upper part of the housing 60.

According to such a PET apparatus 10, a rise in temperature of the detectors 21 is effectively inhibited by the cooling apparatus 50 to keep the detectors 21 at a low temperature, and therefore the time resolution and the energy resolution of the detectors 21 are improved.

The opening edge 40b separating the first air passage 41 and the second air passage 42 may be provided with a passage hole so that the first air passage 41 and the second air passage 42 communicate with each other. Further, the opening edge 40b may be removed so that the first air passage 41 and the second air passage 42 are integrated into one air passage.

This embodiment has the following effect in addition to the above described effects (1) to (10).

(11) According to the radiological imaging apparatus of this embodiment, the entire unit board 20 is housed in the housing 60, and therefore an excellent light blocking characteristic is achieved, and the time resolution and the energy resolution of the detectors 21 are still further improved along with the cooling effect by the cooling apparatus 50.

In the above embodiments, the mounting (housing) of the detector units 2 in the imaging apparatus 11 is not limited to mounting (housing) by the above described unit supporting portion 40, and any mounting/housing means/method may be used.

Figure 8:
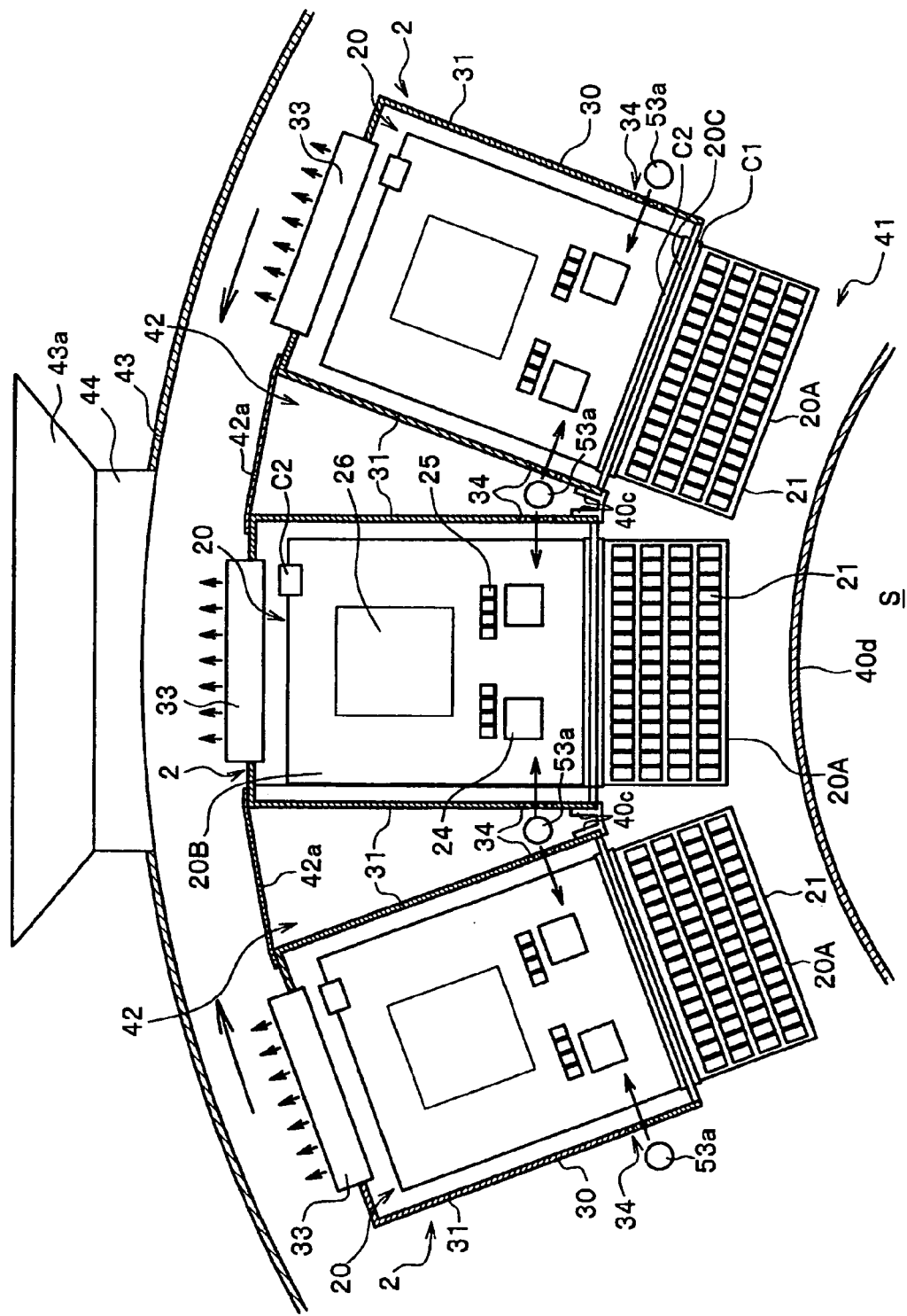
FIG. 8 is a sectional view showing an alternative example of a state in which the detector unit is mounted on the unit supporting portion.

In the above described embodiments, air is fed from the detector space A to the signal processing circuit space B, but the present invention is not limited thereto, and for example, as shown in FIG. 8, cooling air may be fed by the cooling apparatus to only the signal processing circuit space B in which the integrated circuits (digital ASIC and the like). FIG. 8 is a sectional view showing a state in which the detector unit is attached to the unit supporting portion according to an alternative example of the radiological imaging apparatus of the present invention.

In this alternative example, the blow portion 53a of the flow divider 53 is placed in the second air passage 42, and cooling air blown from the blow portion 53a is fed to the signal processing circuit space B from the air hole 34, and then discharged to the exhaust duct 43 by the unit fan 33. Namely, in this example, air is fed to only the signal processing circuit space B, and no air is fed to the first air passage 41.

By such a configuration, the signal processing circuit space B having heat generating elements is directly cooled by air without intervention of the detector space A, and therefore also in this case, heat is hard to be transmitted to the detector space A side on which the detectors 21 are placed, along with the effect of blocking of passage of air by the intermediate board 20C, and a rise in temperature of the detectors 21 can effectively be inhibited. Consequently, the detectors 21 can be kept at a low temperature, the time resolution and the energy resolution of the detectors 21 can be improved, and a radiological imaging apparatus capable of performing an accurate diagnosis is obtained. The frequency of failures of integrated circuits and the like placed in the signal processing circuit space B can be reduced, the reliability of the imaging apparatus 11 is improved, and maintenance costs and the like can be reduced.

Further, although not shown in the figure, air may be fed to the detector space A and the signal processing circuit space B independently. By such a configuration, the detector space A and the signal processing circuit space B can be cooled independently, and temperature control of the spaces A and B can be performed strictly. Consequently, for example, the detectors 21 can be kept at a temperature equivalent to room temperature, and the temperature of the signal processing circuit space B can be held at 80° C. or lower. Thus, the detectors 21 can reliably be kept at a low temperature.

In this case, two cooling apparatuses (first and second cooling apparatuses) may be provided independently for each of the spaces A and B. By such a configuration, controllability of temperature can be improved, and temperature control of the spaces A and B can be performed more strictly. The signal processing circuit space B can be prevented from being cooled more than necessary because the detectors 21 are cooled, thus making it possible to improve the cooling efficiency. Further, an advantage that running costs can be reduced although two independent cooling apparatuses are provided is obtained.

The coolant is not limited to air, but a fluid such as water may be used. In this case, components such as water jackets and the like to which cooling water for cooling is fed are placed in the signal processing circuit space B and the integrated circuits (digital ASIC 26 and the like), whereby cooling can be performed.

Figure 9:
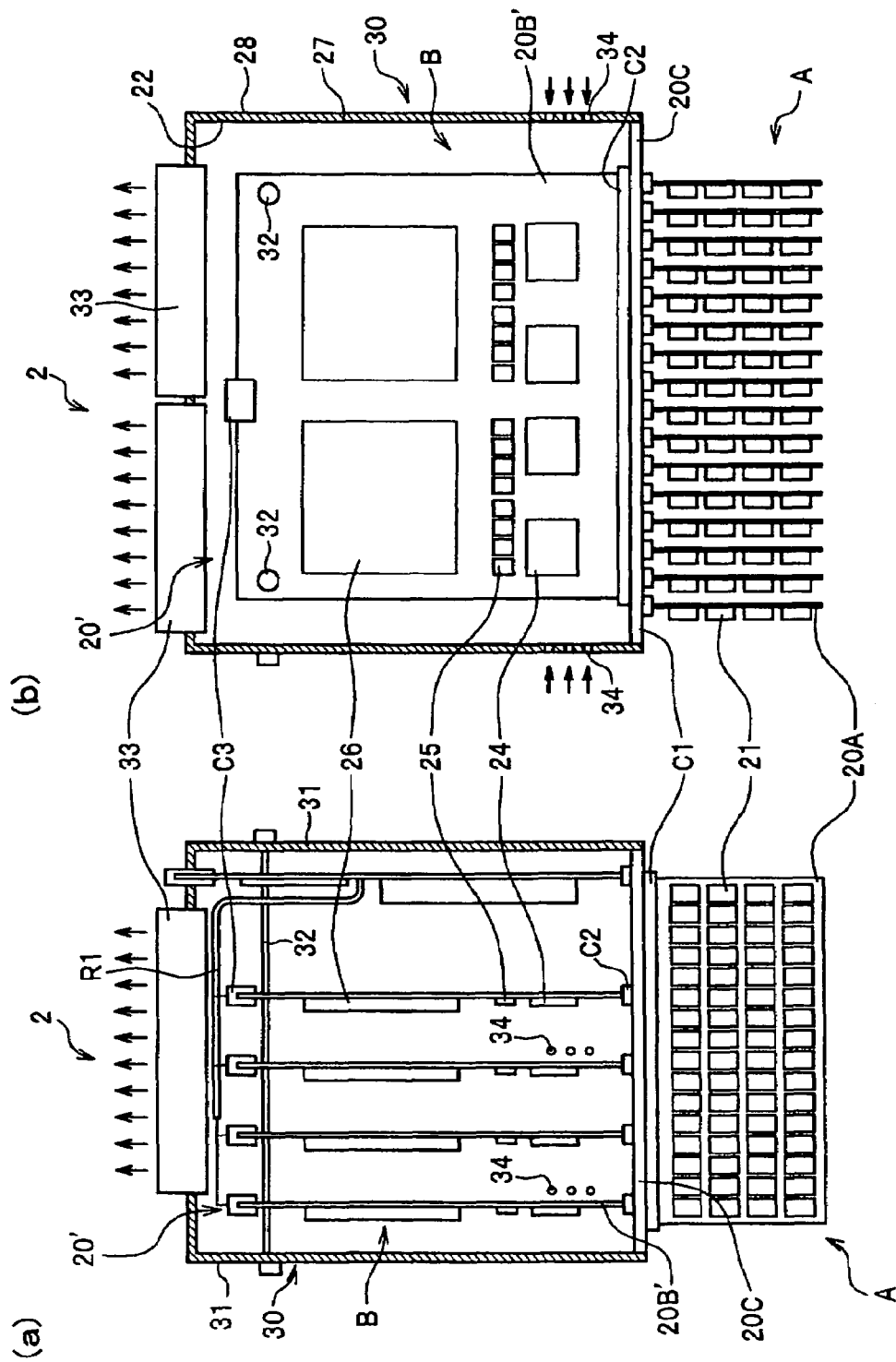

Further, as shown in FIGS. 9(a) and (b), a signal processing board 20B' constituting a unit board 20' may be coupled at an angle of 90 degrees with respect to the detector board 20A. In this configuration, the number of analog ASICs 24, ADs 25 and digital ASICs 26 mounted on the signal processing board 20B' is twice as large as the number of such circuits mounted on the above described signal processing board 20B, whereby four detector boards 20A can electrically be connected to one signal processing board 20B'. Thus, the number of signal processing boards 20B' on the unit board 20' is only the half, and accordingly, the implementation is simplified.

In this example, the air holes 34 are formed in the side parts 31 and 31 opposite in the longitudinal direction of the detector unit 2 so that air flows between the signal processing boards 20B' in accordance to the direction of the signal processing board 20B'. Consequently, in the signal processing circuit space B, air can be made to flow along the surface of the signal processing board 20B'. Thus, efficient cooling of the signal processing circuit space B can be achieved, and an effect of still further improving the time resolution and the energy resolution of the detectors 21 is obtained.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A radiological imaging apparatus comprising:
a bed supporting a testing subject; and
an imaging apparatus imaging said testing subject supported by the bed,
wherein said imaging apparatus has a unit board including:
  a plurality of radiation detectors;
  a signal processing circuit to which detection signals of said radiation detectors are input; and
  an intermediate board existing between said radiation detectors and said signal processing circuit and separating a detector space in which said radiation detectors are placed and a signal processing circuit space in which said signal processing circuit is placed, from each other, and said intermediate board is connected to said radiation detectors and said signal processing circuit separately.

2. The radiological imaging apparatus according to claim 1, comprising a cooling apparatus feeding a coolant to said signal processing circuit space.

3. The radiological imaging apparatus according to claim 2, wherein an inlet of said coolant to said signal processing circuit space is situated near said intermediate board.

4. The radiological imaging apparatus according to claim 3, wherein an outlet for discharging a coolant introduced from said inlet is provided at a position which is opposite to the side on which said intermediate board is placed in said signal processing circuit space, and away from said intermediate board.

5. The radiological imaging apparatus according to claim 4, wherein said outlet is provided at a position opposite to said intermediate board.

6. The radiological imaging apparatus according to claim 1, comprising a cooling apparatus having a passage for feeding the coolant from said detector space to said signal processing circuit space.

7. The radiological imaging apparatus according to claim 1, comprising a first cooling apparatus feeding the coolant to said detector space and a second cooling apparatus feeding the coolant to said signal processing circuit space.

8. The radiological imaging apparatus according to claim 1, wherein said radiation detector is a semiconductor radiation detector.

9. The radiological imaging apparatus according to claim 1, comprising detector units having at least some of a plurality of said unit boards provided in a housing member, wherein a plurality of said detector units are placed around said bed, and said intermediate board separates the inside of said housing member into said detector space and said signal processing circuit space.

10. The radiological imaging apparatus according to claim 9, wherein a part of said unit board where said radiation detectors are present is situated outside said housing member.

11. The radiological imaging apparatus according to claim 9, wherein a part of said housing member consists of said intermediate board.

12. The radiological imaging apparatus according to claim 9,
wherein said imaging apparatus has a cyclic support member surrounding said bed, and a plurality of said detector units are attached to said support member,
said cooling apparatus has a first coolant passage formed inward from said support member and within said imaging apparatus, and a second coolant passage formed outward from said support member and within said imaging apparatus and fed with said coolant in said first coolant passage, and
a part of said detector unit forming said detector space is placed in said first coolant passage, and a part of said detector unit forming said signal processing circuit space is placed in said second coolant passage.

13. The radiological imaging apparatus according to claim 9,
wherein said imaging apparatus has a cyclic support member surrounding said bed, and a plurality of said detector units are attached to said support member,
said cooling apparatus has a first coolant passage formed inward from said support member and within said imaging apparatus, and a second coolant passage formed outward from said support member and within said imaging apparatus and fed with said coolant in said first coolant passage, and
a part of said detector unit forming said signal processing circuit space is placed in said second coolant passage, and a part of said unit board provided in said detector unit, in which said radiation detectors are present, is situated outside said housing member and placed in said first coolant passage.

14. The radiological imaging apparatus according to claim 1, wherein said intermediate board includes a connector (c1) connected to said radiation detector and a connector (c2) connected to said signal processing circuit.

15. A radiological imaging apparatus comprising:
a bed supporting a testing subject; and
an imaging apparatus imaging said testing subject supported by the bed,
wherein said imaging apparatus has a unit board including:

a detector board having a plurality of radiation detectors mounted thereon;

a signal processing board having mounted thereon a signal processing circuit to which detection signals of said radiation detectors are input; and an intermediate board placed between said detector board and said signal processing board and having said detector board and said signal processing board coupled to its opposite surfaces, and a detector space which is formed in said imaging apparatus and in which said radiation detectors are placed and a signal processing circuit space in which said signal processing circuit is placed are mutually separated by said intermediate board.

16. The radiological imaging apparatus according to claim 15, wherein signals from a plurality of said detector boards are processed via the intermediate board by one said signal processing board.

17. The radiological imaging apparatus according to claim 15, comprising a housing member housing at least therein said signal processing board of said unit board, wherein said intermediate board is attached to said housing member.

18. A cooling method of a radiological imaging apparatus comprising an imaging apparatus having a unit board including:

a plurality of radiation detectors;

a signal processing circuit to which detection signals of said radiation detectors are input; and an intermediate board placed between said radiation detectors and said signal processing circuit and separating a detector space in which said radiation detectors are placed and a signal processing circuit space in which said signal processing circuit is placed, from each other, and said intermediate board is connected to said radiation detectors and said signal processing circuit separately, wherein a cooling apparatus is actuated to feed a coolant to said signal processing circuit space.

19. The cooling method of a radiological imaging apparatus according to claim 18, wherein said intermediate board includes a connector (c1) connected to said radiation detector and a connector (c2) connected to said signal processing circuit.

20. The cooling method of a radiological imaging apparatus according to claim 18, wherein a coolant is supplied to said radiation detector space and said signal processing circuit space separately.

21. The cooling method of a radiological imaging apparatus according to claim 18, wherein a coolant is supplied only to said signal processing circuit space.

22. A cooling method of a radiological imaging apparatus comprising an imaging apparatus having a unit board including:

a plurality of radiation detectors;

a signal processing circuit to which detection signals of said radiation detectors are input; and an intermediate board placed between said radiation detectors and said signal processing circuit and separating a detector space in which said radiation detectors are placed and a signal processing circuit space in which said signal processing circuit is placed, from each other, wherein a coolant is fed to said signal processing circuit space, and the coolant fed to said signal processing circuit space is fed from said signal processing circuit space to said detector space.

23. A cooling method of a radiological imaging apparatus comprising:

a bed supporting a testing subject; and an imaging apparatus imaging said testing subject supported by the bed, in which said imaging apparatus has a cyclic support member surrounding said bed, and a plurality of detector units attached to said support member, said detector unit has provided in a housing member a unit board including a plurality of radiation detectors, a signal processing circuit to which detection signals of said radiation detectors are input, an intermediate board placed between said radiation detectors and said signal processing circuit, the radiological imaging apparatus comprises a cooling apparatus having a first coolant passage formed inward from said support member and within said imaging apparatus and a second coolant passage formed outward from said support member and within said imaging apparatus, said intermediate board attached to said housing member separates a detector space in which said radiation detectors are placed and a signal processing circuit space in which said signal processing circuit is placed, and a part of said detector unit forming said detector space is placed in said first coolant passage, and a part of said detector unit forming said signal processing circuit space is placed in said second coolant passage, wherein a coolant is fed to said first coolant passage, and said coolant in said first coolant passage is fed to said second coolant passage.

24. A cooling method of a radiological imaging apparatus comprising:

a bed supporting a testing subject; and an imaging apparatus imaging said testing subject supported by the bed, in which said imaging apparatus has a cyclic support member surrounding said bed, and a plurality of detector units attached to said support member, said detector unit has attached to a housing member a unit board including a plurality of radiation detectors, a signal processing circuit to which detection signals of said radiation detectors are input, an intermediate board placed between said radiation detectors and said signal processing circuit, the radiological imaging apparatus comprises a cooling apparatus having a first coolant passage formed inward from said support member and within said imaging apparatus and a second coolant passage formed outward from said support member and within said imaging apparatus, said intermediate board provided in said housing member separates a detector space in which said radiation detectors are placed and a signal processing circuit space in which said signal processing circuit is placed, and a part of said detector unit forming said detector space is placed in said first coolant passage, and said signal processing circuit of said unit board provided in said detector unit is placed in said second coolant passage, wherein a coolant is fed to said first coolant passage, and said coolant in said first coolant passage is fed to said second coolant passage.

25. The cooling method of a radiological imaging apparatus according to claim 23, wherein said unit board comprises a detector board including said radiation detectors and a signal processing board including said signal processing circuit to which detection signals of said radiation detectors are input.

26. The cooling method of a radiological imaging apparatus according to claim 24, wherein said unit board comprises a detector board including said radiation detectors and a signal processing board including said signal processing circuit to which detection signals of said radiation detectors are input.

* * * * *